US012773349B2

(12) United States Patent
Jørstad

(10) Patent No.: US 12,773,349 B2
(45) Date of Patent: Oct. 27, 2026

(54) MULTI-LUMEN GLAUCOMA STENT

(71) Applicant: Oslo Universitetssykehus HF, Oslo (NO)

(72) Inventor: Øystein Kalsnes Jørstad, Oslo (NO)

(73) Assignee: Oslo Universitetssykehus HF, Oslo (NO)

( * ) Notice: Subject to any disclaimer, the term of this patent is extended or adjusted under 35 U.S.C. 154(b) by 334 days.

(21) Appl. No.: 18/038,400

(22) PCT Filed: Nov. 23, 2021

(86) PCT No.: PCT/IB2021/000823
§ 371 (c)(1),
(2) Date: May 23, 2023

(87) PCT Pub. No.: WO2022/112844
PCT Pub. Date: Jun. 2, 2022

(65) Prior Publication Data

US 2023/0414409 A1 Dec. 28, 2023

Related U.S. Application Data

(60) Provisional application No. 63/118,113, filed on Nov. 25, 2020.

(51) Int. Cl.
*A61F 9/007* (2006.01)
*A61L 31/04* (2006.01)
*A61M 25/00* (2006.01)

(52) U.S. Cl.
CPC ........ *A61F 9/00781* (2013.01); *A61L 31/045* (2013.01); *A61M 25/0028* (2013.01)

(58) Field of Classification Search
CPC ................ A61F 9/00781; A61F 9/0017; A61F 2009/00891; A61F 9/007; A61F 2/15; A61F 2/82; A61F 2/95; A61F 9/00802; A61M 27/002; A61M 2210/0612; A61M 2205/04; A61M 2205/3334; A61M 2205/3341
See application file for complete search history.

(56) References Cited

U.S. PATENT DOCUMENTS 5,433,701 A * 7/1995 Rubinstein .......... A61F 9/00781 604/9
5,558,630 A 9/1996 Fisher
(Continued)

FOREIGN PATENT DOCUMENTS

CN 105997341 A * 10/2016 ............. A61F 9/007
CN 106726124 B * 8/2023 ......... A61F 9/00781
WO WO 2017/181836 10/2017

OTHER PUBLICATIONS

Membrane noun—Oxford Advanced Learner's Dictionary. https://www.oxfordlearnersdictionaries.com/us/definition/english/membrane. Accessed Oct. 2, 2025. (Year: 2025).*
(Continued)

*Primary Examiner* — Adam Marcetich
(74) *Attorney, Agent, or Firm* — Casimir Jones, S.C.; J Mitchell Jones

(57) ABSTRACT

The present invention relates to stents for the relief of intraocular pressure in patients with glaucoma and in particular to stents with one or more sealed channels, which may be opened following placement of the stent.

18 Claims, 10 Drawing Sheets

(56) References Cited

U.S. PATENT DOCUMENTS 5,626,558 A * 5/1997 Suson ................. A61F 9/00781 604/9
6,007,511 A 12/1999 Prywes
6,544,249 B1 4/2003 Yu et al.
6,558,342 B1 * 5/2003 Yaron ................. A61F 9/00781 604/9
8,663,303 B2 3/2014 Horvath et al.
8,721,702 B2 5/2014 Romoda et al.
8,765,210 B2 7/2014 Romoda et al.
8,852,136 B2 10/2014 Horvath et al.
8,852,256 B2 10/2014 Horvath et al.
9,017,276 B2 4/2015 Horvath et al.
9,095,413 B2 8/2015 Romoda et al.
9,113,994 B2 8/2015 Romoda et al.
9,192,516 B2 11/2015 Horvath et al.
2003/0236483 A1 * 12/2003 Ren ..................... A61F 9/00781 606/107
2004/0162545 A1 * 8/2004 Brown ................ A61F 9/00781 977/778
2004/0254521 A1 * 12/2004 Simon ................. A61F 9/00781 604/8
2005/0087520 A1 * 4/2005 Wang ................... B23K 26/361 219/121.69
2005/0119737 A1 * 6/2005 Bene ................... A61F 9/00781 623/4.1
2007/0156079 A1 7/2007 Brown
2008/0108933 A1 5/2008 Yu et al.
2009/0196903 A1 * 8/2009 Kliman ................... A61P 27/02 424/423
2011/0105986 A1 * 5/2011 Bronstein ........... A61F 9/00781 604/8
2013/0267887 A1 * 10/2013 Kahook .............. A61F 9/00781 604/9
2014/0236066 A1 * 8/2014 Horvath .................. A61L 31/08 604/9
2015/0265469 A1 * 9/2015 Olson ................. A61F 9/00781 604/8
2017/0071791 A1 * 3/2017 Piven ........................ A61F 2/15
2017/0087016 A1 * 3/2017 Camras ............... A61F 9/00781
2017/0367888 A1 * 12/2017 Brown .................... A61L 27/18
2018/0263819 A1 * 9/2018 Roeber ................. A61L 31/048
2019/0254873 A1 * 8/2019 Camras ................ A61K 9/0051
2020/0229977 A1 * 7/2020 Mixter ................ A61F 9/00781
2020/0229979 A1 * 7/2020 Otaka ...................... A61F 9/008
2020/0229982 A1 * 7/2020 Mixter ................ A61F 9/00781
2021/0161713 A1 * 6/2021 Bouremel ............... B29C 48/11
2023/0218441 A1 * 7/2023 Hacker ..................... A61F 2/82 604/8

OTHER PUBLICATIONS

American Heritage Dictionary Entry: membrane. https://www.ahdictionary.com/word/search.html?q=membrane. Accessed Oct. 2, 2025. (Year: 2025).*

International Search Report and Written Opinion for PCT/IB2021/000823. Mailed Apr. 4, 2022. 15 pages.

* cited by examiner

MULTI-LUMEN GLAUCOMA STENT

FIELD OF THE INVENTION

The present invention relates to stents for the relief of intraocular pressure in patients with glaucoma, and in particular to stents with one or more sealed channels that may be opened following placement of the stent.

BACKGROUND OF THE INVENTION

Glaucoma is a group of eye diseases characterized by optic neuropathy, which may or may not be accompanied by raised intraocular pressure (IOP). Glaucoma is the leading cause of irreversible blindness in the world. The primary goal of treatment is to lower the IOP by means of medicines or surgical procedures.

Drainage of aqueous fluid is the cornerstone of glaucoma surgery. In this regard there is a trend towards replacing conventional trabeculectomy with stents, so-called micro-invasive glaucoma surgery (MIGS). This surgical option is particularly appealing to treat patients in the gap between early and advanced glaucoma. Notably, when draining fluid from the anterior chamber to a second reservoir, the anterior chamber pressure is regulated by the combined outflow resistance through the stent and out of the second reservoir.

The first MIGS device approved by the US Food and Drug Administration was the iStent (Glaukos; CA, USA). The iStent creates a bypass pathway through the trabecular meshwork. The remaining outflow resistance is provided by the scleral aqueous channels and intrascleral veins. As each stent increases the access to collector channels and fluid outflow, an additional reduction in IOP can be seen after implantation of two or more devices. Theoretically, the iStent has a lower limit for reducing the IOP similar to the episcleral venous pressure, which is approximately 10 mm Hg.

An alternative to bypassing the trabecular meshwork is to create a subconjunctival drainage pathway. In contrast to the scleral aqueous channels, a healthy conjunctiva provides minimal subconjunctival outflow resistance, and the potential for reducing the intraocular pressure is therefore higher than that of the iStent. An example of a device that creates drainage into the subconjunctival space is the XEN®45 Gel Stent (Allergan; Dublin, Ireland). This stent and devices for its insertion are described in U.S. Pat. Nos. 6,007,511; 8,663,303; 8,721,702; 8,765,210; 8,852,136; 8,852,256; 9,017,276; 9,192,516; 9,095,413; 9,113,994; each of which is incorporated by reference herein in its entirety.

A second alternative to bypassing the trabecular meshwork is to create a suprachoroidal drainage pathway, which utilizes the pressure difference between the anterior chamber and the suprachoroidal space to lower the TOP.

Inevitably, the necessary outflow resistance of a tube draining subconjunctivally restricts its full TOP lowering potential. Consequently, the target TOP may not be met. Moreover, glaucoma is a chronic disease, and the TOP may increase over time despite an initially successful stent procedure. The trend towards MIGS stents in glaucoma notwithstanding, additional surgical or medical therapy is often necessary and increases the burden of treatment. The present invention solves this problem by providing a multilumen stent with sealed secondary channels, which may be opened according to need to further lower the outflow resistance of the stent and, thus, the TOP.

SUMMARY OF THE INVENTION

The present invention relates to stents for the relief of TOP in patients with glaucoma, and in particular to stents with one or more sealed secondary channels, which may be opened following placement of the stent.

In some preferred embodiments, the present invention provides glaucoma microstents for minimally invasive glaucoma surgery comprising: a microstent with proximal and distal ends, the microstent having therein at least one open channel that extends between the proximal and distal ends, at least one open channel having openings at both the proximal and distal ends to allow fluid flow therethrough, the microstent further having therein at least one sealed channel that extends between the proximal and distal ends, the at least one sealed channel having an opening at the distal end and a seal at the proximal end to prevent fluid flow therethrough.

In some preferred embodiments, the microstent comprises from 2 to 7 sealed channels. In some preferred embodiments, the microstent comprises one open channel.

In some preferred embodiments, the microstent comprises from 2 to 5 sealed channels. In some preferred embodiments, the microstent comprises one open channel.

In some preferred embodiments, the microstent comprises from 2 to 3 sealed channels. In some preferred embodiments, the microstent comprises one open channel.

In some preferred embodiments, the microstent comprises 2 sealed channels. In some preferred embodiments, the microstent comprises one open channel.

In some preferred embodiments, each of the channels of the microstent is sized to provide a flow resistance of from 0.5 to 8.0 mm Hg.

In some preferred embodiments, each of the channels of the microstent is sized to provide a flow resistance of from 0.5 to 5.0 mm Hg.

In some preferred embodiments, each of the channels of the microstent is sized to provide a flow resistance of from 0.5 to 3.5 mm Hg.

In some preferred embodiments, the combined channels in the microstent provide a flow resistance of from 0.5 to 10 mm Hg when open.

In some preferred embodiments, the channels in the microstent are parallel. In some preferred embodiments, the channels in the microstent are circular in cross section. In some preferred embodiments, the microstent is tubular in shape. In some preferred embodiments, the proximal end of the stent comprises a rim portion that extends past the terminal ends of the channels.

In some preferred embodiments, the microstent is formed from a polymer. In some preferred embodiments, the polymer is selected from the group consisting of silicone, cross-linked polyvinyl alcohol (PVA) hydrogel, cross-linked PVA hydrogel foam, polyurethane, polyamide, styrene isobutylene-styrene block copolymer (Kraton), polyethylene terephthalate, polyester, polyorthoester, polyanhydride, polyether sulfone, polycarbonate, polypropylene, high molecular weight polyethylene, and polytetrafluoroethylene.

In some preferred embodiments, the stent is formed from a gel material. In some preferred embodiments, the gel material is a cross-linked gelatin.

In some preferred embodiments, the stent is 3D printed in a suitable biocompatible material.

In some preferred embodiments, the seal is a membrane. In some preferred embodiments, the membrane is formed from a material selected from the group consisting of silicone, polyurethane, polyamide, styrene isobutylene-styrene block copolymer (Kraton), polyethylene terephthalate, polyester, polyorthoester, polyanhydride, polyether sulfone, polycarbonate, polypropylene, high molecular weight polyethylene, and polytetrafluoroethylene.

In some preferred embodiments, said membrane is non-transparent or opaque. In some preferred embodiments, said membrane is colored to enhance absorption of the light wave emitted from a laser.

In some preferred embodiments, the present invention provides methods of treating glaucoma in a subject in need thereof comprising: inserting a glaucoma microstent as described above into the eye of a subject so that the proximal end of the microstent is located in the anterior chamber of the eye and the distal end is located in a portion of the eye allowing drainage into the subconjunctival space of the eye so that intraocular pressure in the anterior chamber is reduced due to the flow of fluid through the open channel of the glaucoma microstent. In some preferred embodiments, the portion of eye allowing drainage into the subconjunctival space is the intra-Tenon's space. In some preferred embodiments, the methods further comprise the step of applying energy to the seal at the proximal end of one or more of the sealed channels to ablate the seal thereby allowing fluid flow from the previously sealed channel to further decrease intraocular pressure. In some preferred embodiments, the methods further comprise evaluating TOP prior to removal of the seal. In some preferred embodiments, the methods further comprise removing seals from the channels in a serial manner to achieve a desired reduction of TOP. In some preferred embodiments, the microstent is inserted with an ab interno approach.

In some preferred embodiments, the present invention provides a combined microstent and injection device comprising a microstent as described above inserted into a hollow shaft having a proximal end and a distal end. In some preferred embodiments, the microstent is positioned in the hollow shaft so that the distal end of the microstent is aligned with the distal end of the hollow shaft. In some preferred embodiments, the proximal end of the hollow shaft is connected to an ejector and the distal end is configured to allow ejection of the microstent from the hollow shaft upon deployment of the ejector. In some preferred embodiments, the device is provided in a sterile package.

DETAIL DESCRIPTION OF THE INVENTION

The present invention relates to stents for the relief of IOP in patients with glaucoma, and in particular to stents with one or more sealed secondary channels that may be opened following placement of the stent.

Figure 1:
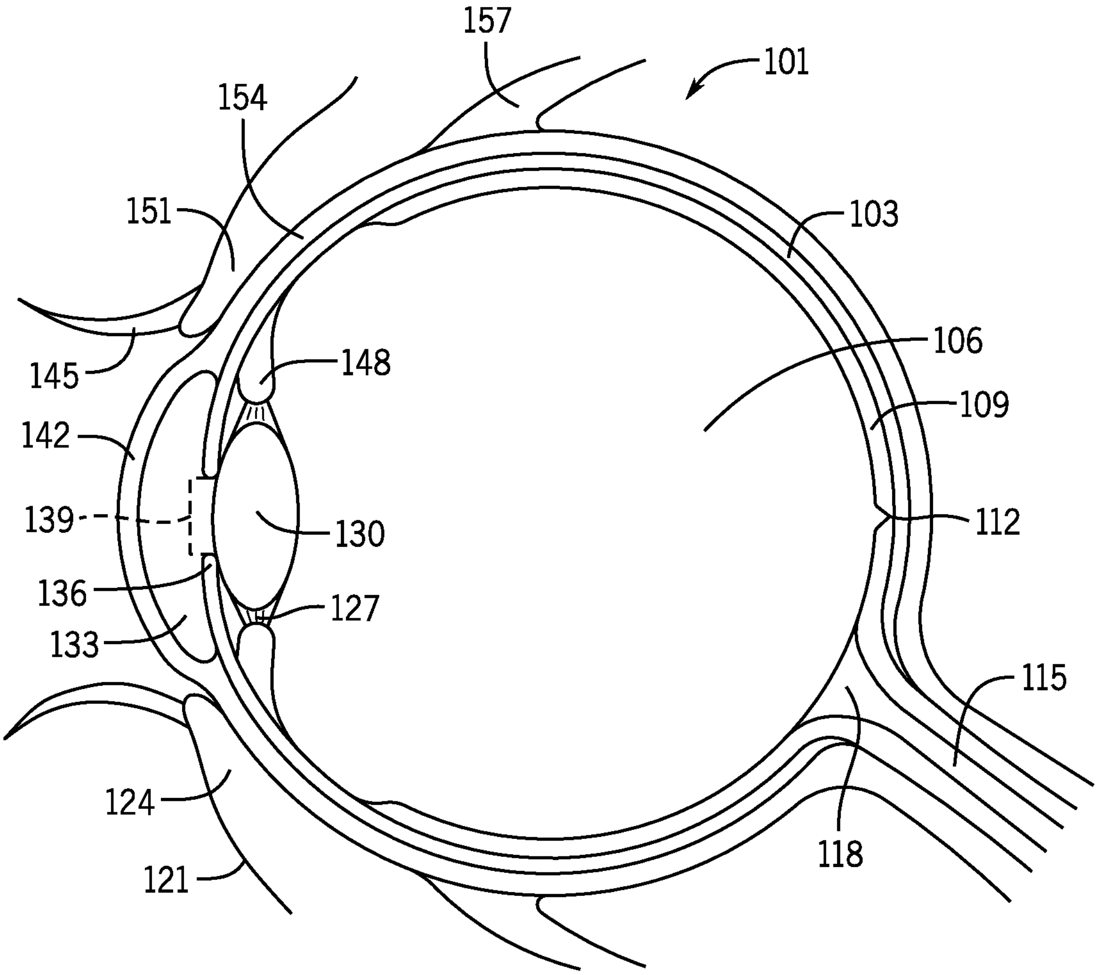
FIG. 1 is a schematic cross-sectional view of a human eye showing various structures of the eye.

FIG. 1 provides a cross-section of a human eye 101. The main structural features are: the choroid 103; vitreous humor 106; retina 109; fovea 112; optic nerve 115; blind spot 118; conjunctiva 121; subconjunctival space 124; suspensory ligament 127; lens 130; anterior chamber 133; iris 136; pupil 139; cornea 142; eyelash 145; ciliary body 148; eyelid 151; sclera 154; and rectus muscle 157. The anterior chamber 133 is filled with aqueous humor 106. The aqueous humor 106 drains into a space(s) 124 below the conjunctiva 121 through the trabecular meshwork (not shown in detail) of the sclera 154. The aqueous humor is drained from the space(s) 124 below the conjunctiva 121 through a venous drainage system (not shown).

Figure 2:
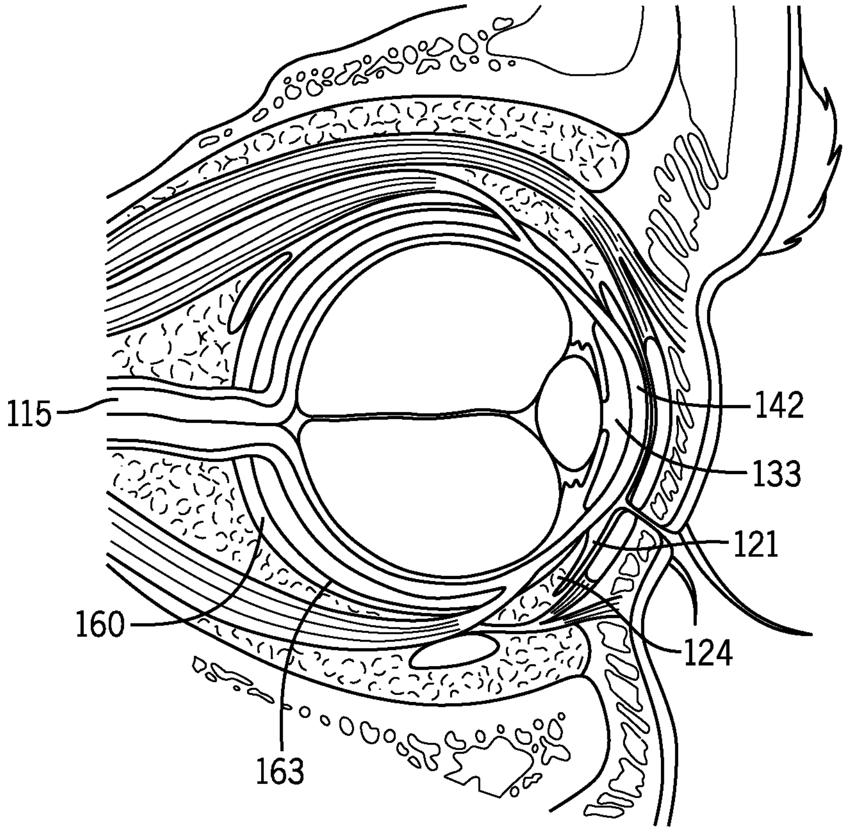
FIG. 2 is a schematic cross-sectional view of a human eye showing specific anatomical landmarks, including the Tenon's space and subconjunctival space.

FIG. 2 shows the relationship of the conjunctiva 121 and Tenon's capsule 160 and sub-Tenon's space 163. Tenon's capsule 160 is a fascial layer of connective tissue surrounding the globe and extra-ocular muscles. As shown in FIG. 2, it is attached anteriorly to the limbus of the eye and extends posteriorly over the surface of the globe until it fuses with the dura surrounding the optic nerve 115. The conjunctiva 121 and Tenon's capsule 160 are separate membranes that start at the limbal fusion and connect to tissue at the posterior of the eye. The space formed below the conjunctiva 121 is referred to as the subconjunctival space 124. Below Tenon's capsule 160 there are Tenon's adhesions that connect the Tenon's capsule 160 to the sclera 11. The space between Tenon's capsule 160 and the sclera where the Tenon's adhesions connect the Tenon's capsule 160 to the sclera is referred to as the intra-Tenon's space.

Glaucoma is a group of eye diseases that damage the optic nerve. A main risk factor for glaucoma is elevated IOP. Elevated IOP is due to a buildup of a fluid (aqueous humor) that flows throughout the inside of the eye. This internal fluid normally drains out through a tissue called the trabecular meshwork at the angle where the iris and cornea meet. When fluid is overproduced or the drainage system doesn't work properly, the fluid can't flow out at its normal rate and the IOP increases. Glaucoma commonly affects both eyes, and without appropriate IOP-lowering treatment, it progressively damages the visual field and results in tunnel vision and ultimately blindness.

Various stents have been developed to relieve IOP to treat glaucoma in a procedure known as micro-invasive glaucoma surgery (MIGS). One example of a glaucoma stent is the XEN® Gel stent (Allergan; Dublin, Ireland), see, e.g., U.S. Pat. Nos. 6,007,511; 8,663,303; 8,721,702; 8,765,210; 8,852,136; 8,852,256; 9,017,276; 9,192,516; 9,095,413; 9,113,994; each of which is incorporated by reference herein in its entirety. Regardless of stent type, the crucial goal of MIGS is to provide sufficient long-term outflow of fluid without causing ocular hypotony. Because of its minimal outflow resistance, the risk of hypotony is particularly relevant when draining fluid to the subconjunctival space. Accordingly, the outflow resistance through the stent must provide a sufficient safety margin.

Current glaucoma stents used for MIGS generally comprise a single channel. Inevitably, the necessary outflow resistance of a tube draining subconjunctivally restricts its full IOP lowering potential. Consequently, the target IOP may not be met. Moreover, glaucoma is a chronic disease, and the IOP can increase over time despite an initially successful stent procedure. The trend towards MIGS stents in glaucoma notwithstanding, additional surgical or medical therapy is often necessary and increases the burden of treatment.

The present invention addresses this problem by providing a novel glaucoma stent for MIGS with multiple channels wherein one or more of the channels are reversibly sealed so that the sealed channel may be opened at a later time by means of a simple laser procedure to allow additional IOP relief. In this way, the IOP lowering potential of the original MIGS procedure can be heightened stepwise according to need, thereby improving the prospect of the stent for successful long-term glaucoma monotherapy without hypotony. Because opening of each secondary channel will further decrease the outflow resistance, the efficacy of the stent can be up-titrated with a minimally invasive laser procedure to safely achieve the desired TOP.

Figure 3A:
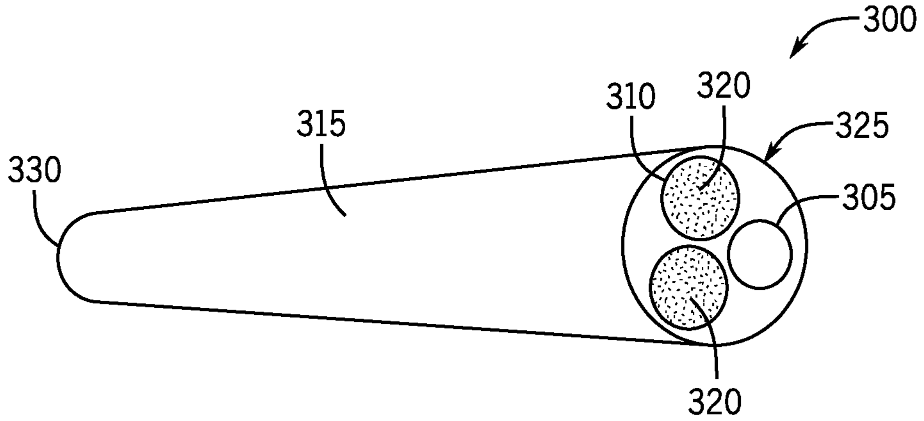
FIGS. 3A and 3B are perspective views of a microstent of the present invention.
Figure 3B:
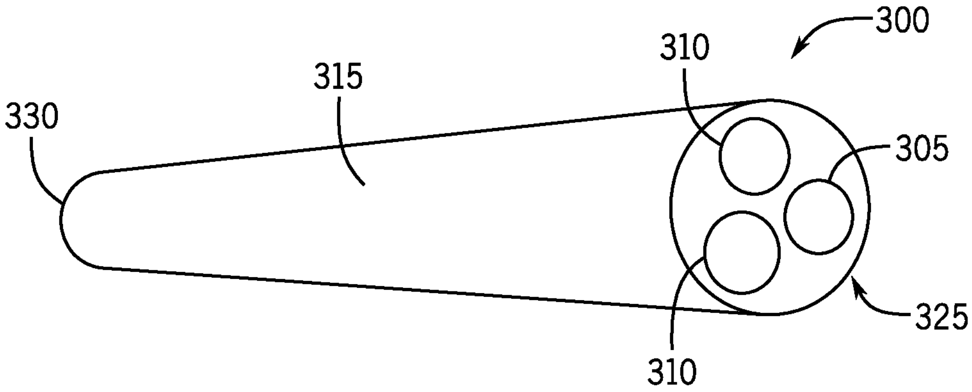

As depicted in FIGS. 3A and 3B, instead of a conventional single channel (or lumen) design, in some embodiments the novel stent of the present invention 300 has one primary channel 305 and several secondary channels (or lumina) 310. In general, the stent of the present invention further comprises an elongated stent body 315 having a proximal end 325 and a distal end 330. The channels 305 and 310 extend the length of the stent body 315 to provide channels therethrough. In some preferred embodiments, the secondary channels comprise a seal 320 at the proximal end 325 of the stent body 315. Thus, in preferred embodiments, only the primary channel 305 is open by default. The opening of each secondary channel, which as described in more detail below is positioned in the eye's anterior chamber, is sealed, preferably with a thin membrane that is impermeable to fluids. It is contemplated that should the primary channel fail to meet the target TOP, the thin membrane sealing each secondary lumen can be opened independently (e.g., laser ablated) by application of energy from a suitable source. Suitable sources of energy include but are not limited to argon or YAG lasers. FIG. 3B provide a depiction of a microstent of the present invention in which the seals 320 shown in FIG. 3A have been removed.

The size of the primary and secondary channels may be varied to provide desired fluid flow levels and TOP reduction. Appropriate channel dimensions can be determined using the Hagen-Poiseuille equation; the depending factors are the length and inner diameter of the tube, the aqueous fluid production rate (approximately 2 μl/min), and the aqueous fluid viscosity (approximately 0.72 mPa·s at 36° C.). In some preferred embodiments, the channels (and thus the microstent) are from about 2 to 10 mm in length, preferably from about 4 to 8 mm in length and most preferably about 6 mm in length. In some preferred embodiments, the inner diameter of the channels is from about 10 to 60 μm, more preferably from about 20 to 50 μm, and most preferably from about 35 to 50 μm. In any event, it will be recognized that the length and diameter may be varied to provide the preferred fluid flow. Thus, in some embodiments, each of the channels are sized to provide a flow resistance from to 8.0 mm Hg, more preferably from 0.5 to 5.0 mm Hg, and most preferably from 0.5 to 3.5 mm Hg. In some embodiments, the combined channels provide a total flow resistance of the stent from 0.5 to 20 mm Hg, more preferably from 0.5 to 15 mm Hg, and most preferably from 0.5 to 10 mm Hg.

Figure 4A:
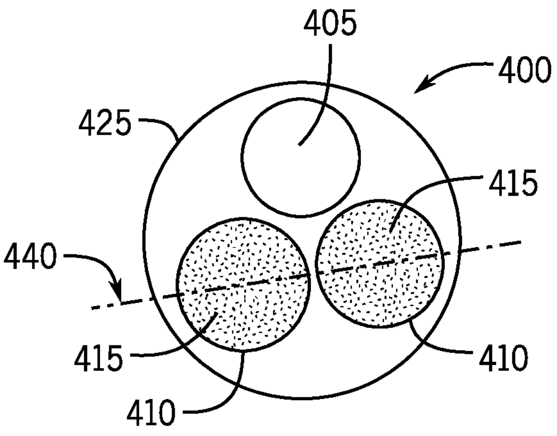
FIGS. 4A, 4B and 4D are ends views of a microstent of the present invention.
Figure 4B:
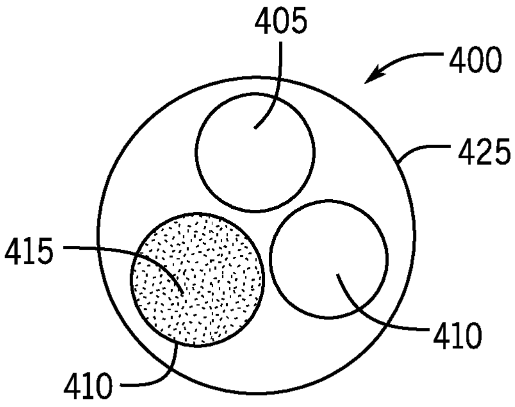
Figure 4C:
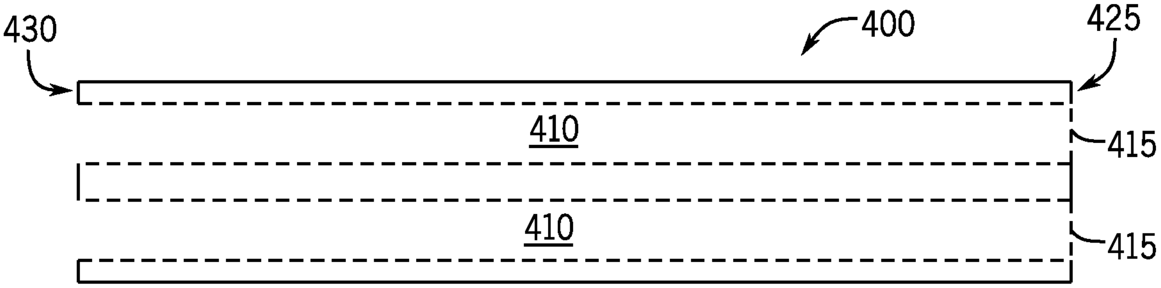
FIG. 4C is a cross-sectional view of a microstent of the present invention along line 440 in FIG. 4A.
Figure 4D:
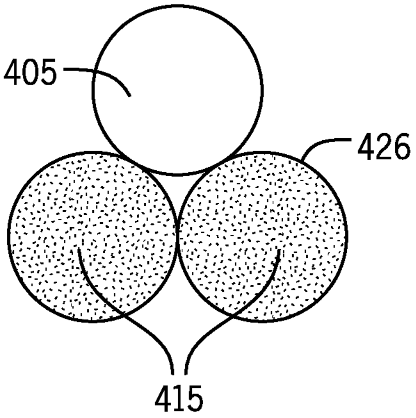

FIGS. 4A and 4B provide end views of microstent 400 of the present invention. As shown in FIG. 4A, the proximal end 425 of the microstent 400 comprises an open primary channel 405 and sealed secondary channels 410 comprising seals 415. As shown in FIG. 4B, the proximal end 425 of the microstent 400 comprises an open primary channel 405 and one secondary channel 410 in which the seal has been removed and another secondary channel 410 with the seal 415 still in place. FIG. 4C provides a cross-sectional view of a microstent 400 of the present invention taken along the line 440 in FIG. 4A. The secondary channels 415 each comprise a seal 415 at the proximal end 425 of the microstent 400. The distal end is indicated by 430. In some alternative embodiments, the stents of the present invention may be formed by attaching multiple tubes 426 together as visualized by FIG. 4D.

Figure 5A:
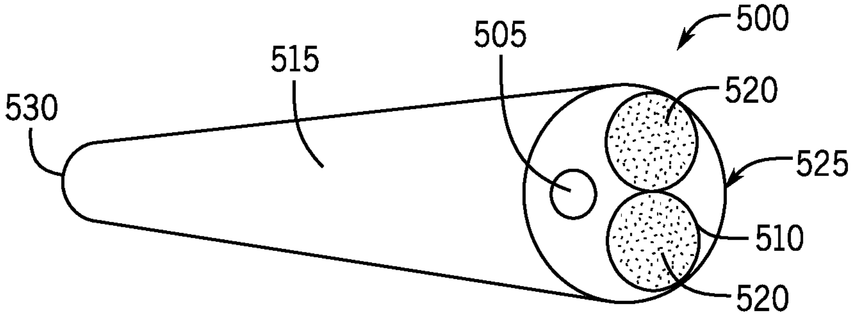
FIGS. 5A and 5B are perspective views of additional microstent embodiments of the present invention.
Figure 5B:
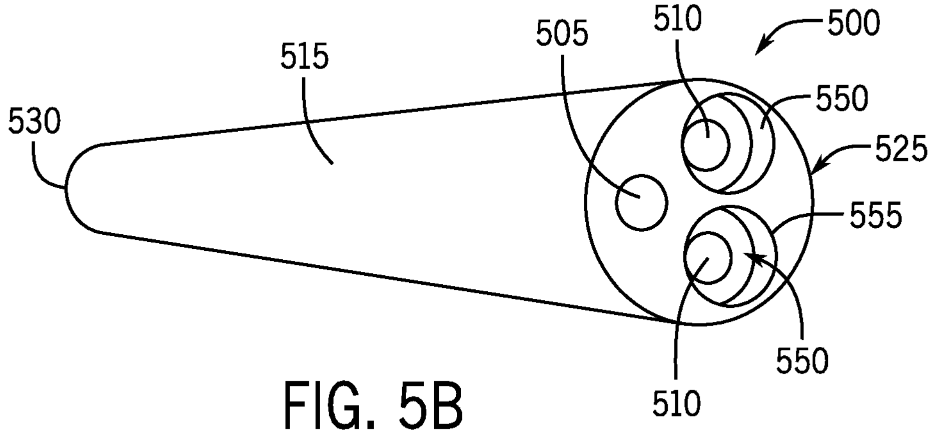
Figure 6:
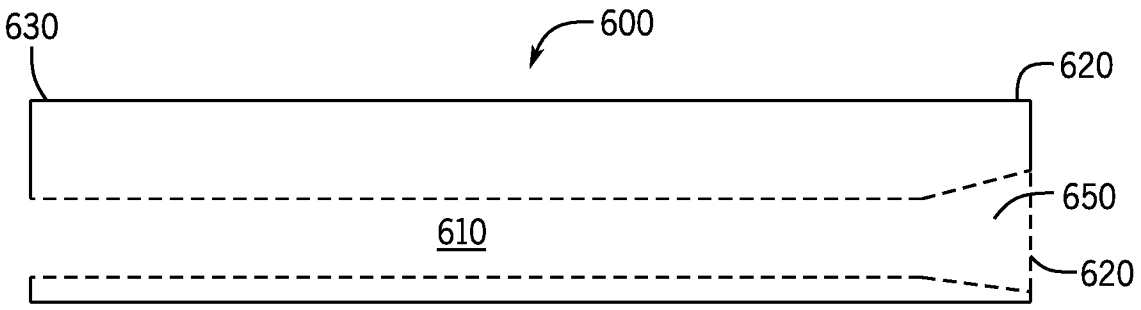
FIG. 6 is a cross-sectional view of an additional embodiment of a microstent of the present invention.

FIGS. 5A and 5B depict alternative embodiments of microstents 500 of the present invention. In this embodiment, the primary channel 505 extends through the elongated microstent body 515 from the proximal end 525 of the microstent 500 to the distal end 530 of the microstent 500 so that fluid can flow therethrough. As depicted in FIG. 5A, the secondary channels comprise seals 520 at the proximal end 525 of the microstent 500. As depicted in FIG. 5B, the seals 520 depicted in FIG. 5A have been removed. As further depicted in FIG. 5B, the secondary channels 510 are recessed in opening 550 formed by the rim portion 555 so that diameter of the opening 550 is greater than the diameter of the secondary channel 510. It is contemplated that for standard argon laser trabeculoplasty, the diameter of the laser spot is typically 50 μm. Thus, in preferred embodiments, the membrane sealing each secondary lumen in the eye's anterior chamber should have at least similar dimensions to facilitate focusing the laser; therefore, the opening at the proximal ends of the two secondary channels can be sized to accommodate standard laser spot diameters, whereas the secondary channel itself may have a smaller diameter. A cross-sectional view corresponding to this embodiment is provided in FIG. 6 which depicts a microstent 600 having proximal end 625 and distal end 630 with a secondary channel 610 extending therebetween. A seal 620 is located at the proximal end of the secondary channel 610. The secondary channel 610 has an opening 650 therein that is wider than the secondary channel itself 610.

Figure 7:
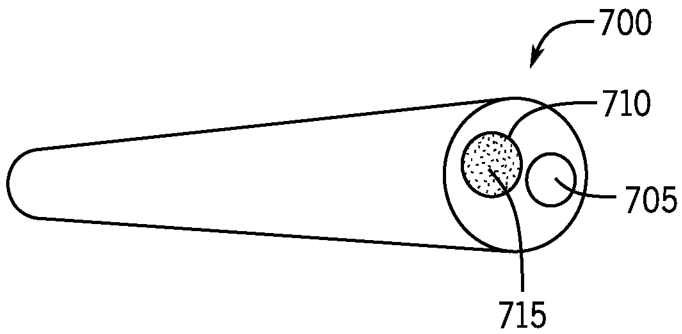
FIG. 7 is a perspective view of an additional microstent embodiment of the present invention.
Figure 8:
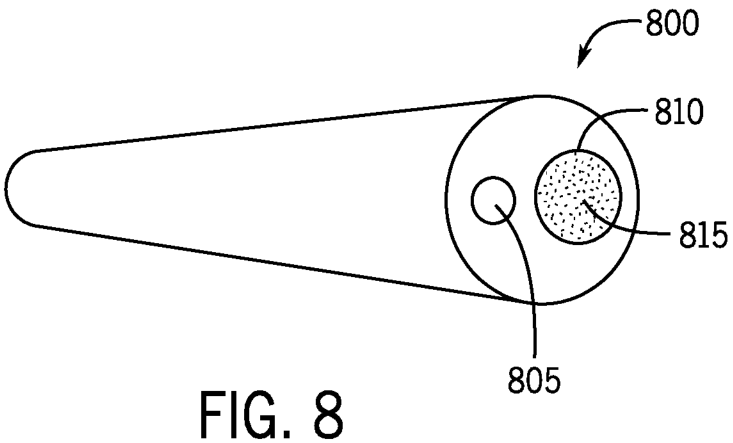
FIG. 8 is a perspective view of an additional microstent embodiment of the present invention.
Figure 9:
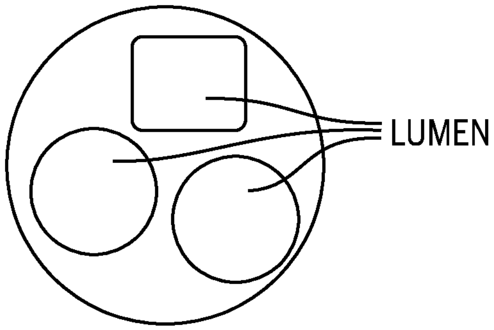
FIG. 9 is a schematic depiction of different channel shapes in a microstent of the instant invention.

FIGS. 7, 8 and 9 provide depictions of different embodiments of certain aspects of the microstents of the present invention. As shown in FIGS. 7 and 8, microstents (e.g., 700 and 800) are not limited to any particular number of primary and secondary or sealed channels. FIGS. 7 and 8 depict microstents with one primary channel (705 and 805) and one secondary channel (710 and 810) comprising a seal (715 and 815). The present invention is not limited to the microstents with any particular number of primary and secondary channels. In some embodiments, the microstent comprises from 2 to 7 sealed channels, while in other embodiments, the microstent comprise from either 2 to 5 sealed channels or from 2 to 3 sealed channels. In some embodiments, the microstents comprise 1, 2 or 3 open primary channels. As described above, whatever the number of channels, the channels are preferably sized to provide a flow resistance of from 0.5 to 8.0 mm Hg, more preferably from 0.5 to 5.0 mm Hg, and most preferably from 0.5 to 3.5 mm Hg for each channel and a total flow resistance for the microstent of from 0.5 to 20 mm Hg, more preferably from 0.5 to 15 mm Hg, and most preferably from 0.5 to 10 mm Hg. As shown in FIG. 9, the cross-sectional shape of the primary and secondary channels of the present invention is not limited.

While in preferred embodiments, the channels are circular in cross-section, the channels may also be oval, square, rectangular, or triangular in cross section.

The microstents of the present invention may be formed from any suitable material. In some embodiments, the microstents are formed from a biocompatible polymer or other biocompatible material. Suitable biocompatible materials and polymers include, but are not limited to, cross-linked gelatin hydrogel (e.g., cross-linked with glutaraldehyde), silicone, cross-linked polyvinyl alcohol (PVA) hydrogel, cross-linked PVA hydrogel foam, polyurethane, polyamide, styrene isobutylene-styrene block copolymer (Kraton), polyethylene terephthalate, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as polylactic acid, polyglycolic acid or copolymers thereof, a polyanhydride, polycaprolactone, polyhydroxybutyrate valerate or other biodegradable polymer, or mixtures or copolymers thereof.

The seals utilized in the microstents of the present invention may be formed from any suitable material. In general, the material should be chosen so that it can be ablated by lasers used in optical surgeries such as argon and YAG lasers. In some embodiments, it is contemplated that the laser membranotomy procedure is analogous to routine argon laser trabeculoplasty or YAG laser capsulotomy for posterior capsule opacification. Suitable seals include membranes formed from biocompatible polymers, such as those listed above.

The microstents of the present invention are preferably used to reduce IOP in a subject in need thereof. Suitable subjects include human patients, as well as animal subjects such as companion animals, e.g., dogs, cats, horses, and the like. In some preferred embodiments, the microstents of the present invention are deployed into an eye such that the stent forms a passage from the anterior chamber of the eye to the intra-Tenon's space. Deployment of the stent such that the inlet terminates in the eye's anterior chamber and the outlet terminates in the intra-Tenon's space safeguards the integrity of the conjunctiva to allow subconjunctival drainage pathways to successfully form. The conjunctiva is protected from direct contact with the shunt by Tenon's capsule. Additionally, drainage into the intra-Tenon's space provides access to more lymphatic channels than just the conjunctival lymphatic system, such as the episcleral lymphatic network. Moreover, deployment of the stent so that the outlet terminates in the intra-Tenon's space avoids having to pierce Tenon's capsule which can otherwise cause complications during glaucoma filtration surgery due to its tough and fibrous nature.

Figure 10:
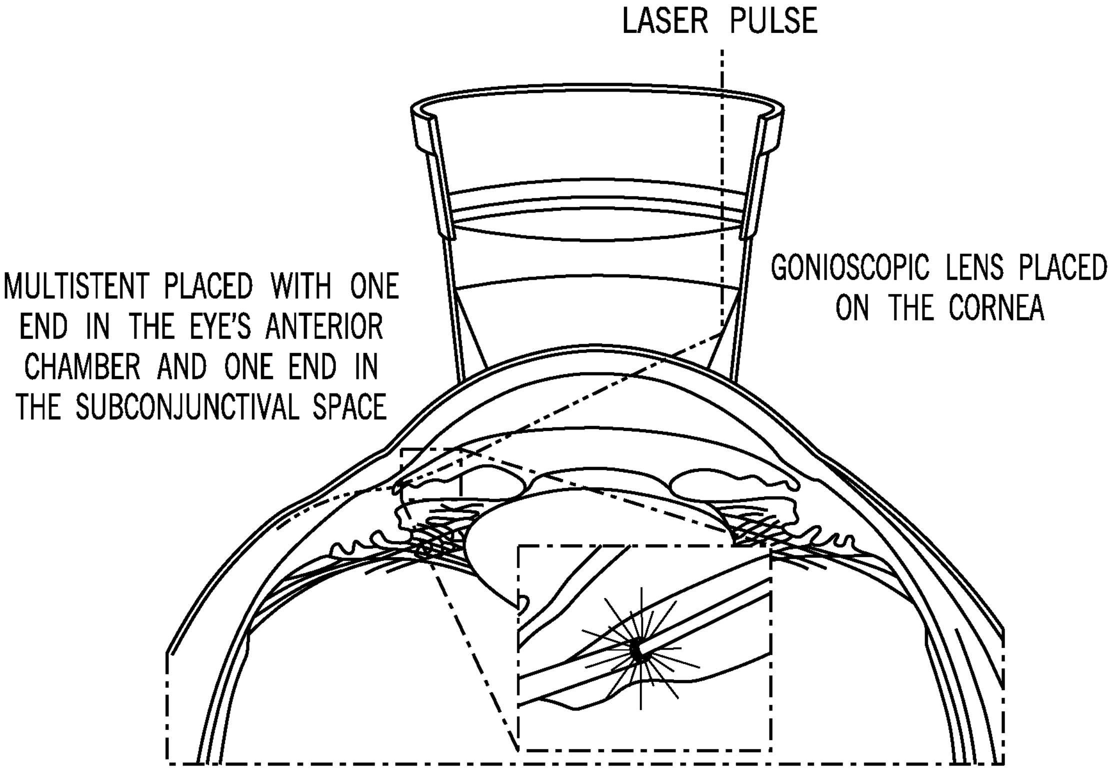
FIG. 10 is a schematic depiction of placement of a microstent of the present invention in a human eye and application of a laser pulse to remove a seal from a secondary channel.

FIG. 10 provides a schematic drawing depicting placement of a microstent of the present invention in the eye of a subject. Specifically, FIG. 10 shows a cross-sectional drawing of the eye's anterior segment with a gonioscopic lens placed on the cornea. The lens allows for visualization of the multilumen stent entering the anterior chamber angle.

In some preferred embodiments, the stents are inserted using an ab interno glaucoma treatment procedure. Ab interno approaches for implanting an intraocular stent in the subconjunctival space are shown for example in Yu et al. (U.S. Pat. No. 6,544,249 and U.S. patent publication number 2008/0108933) and Prywes (U.S. Pat. No. 6,007,511), the contents of each of which are incorporated by reference herein in its entirety. Briefly, a surgical intervention to implant the stent involves inserting into the eye a deployment device that holds the microstent and deploying the stent within the eye. A deployment device holding the stent enters the eye through the cornea (ab interno approach). The deployment device is advanced across the anterior chamber in what is referred to as a transpupillary implant insertion. The deployment device is advanced through the sclera until a distal portion of the device is in proximity to the subconjunctival space. The stent is then deployed from the deployment device, producing a conduit between the anterior chamber and the subconjunctival space to allow aqueous humor to drain through the conjunctival lymphatic system.

Figure 11A:
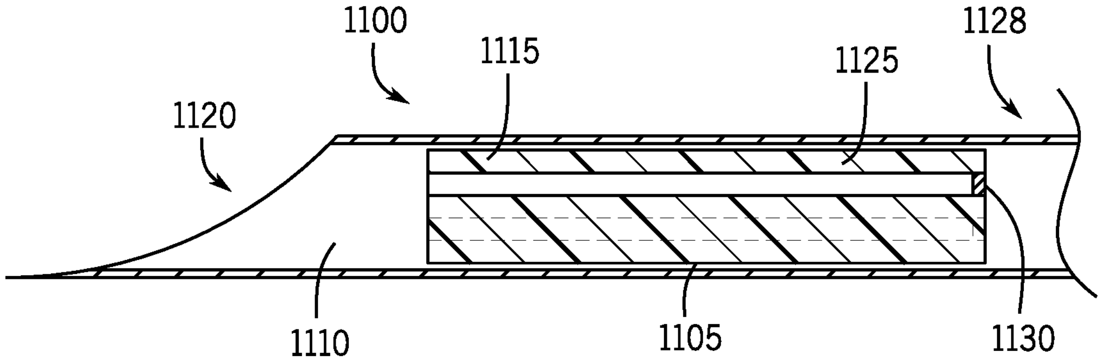
FIG. 11A is a longitudinal section of hollow shaft comprising a stent and FIG. 11B is a cross section of hollow shaft comprising a stent.
Figure 11B:
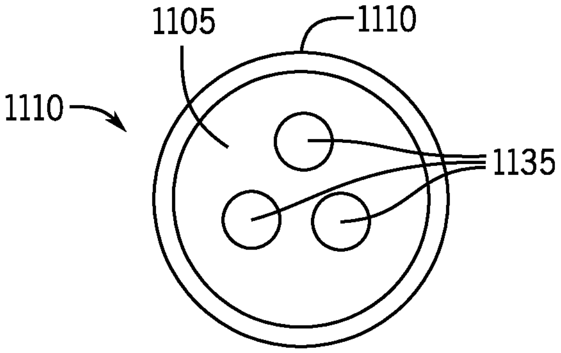

Thus, in some preferred embodiments, the present invention provides a deployment device comprising a hollow shaft configured to hold the microstent, as described herein. In preferred embodiments depicted in FIG. 11A, the deployment device 1100 comprises a microstent 1105 oriented in the hollow shaft 1110 with the distal end 1115 of the microstent positioned in the distal end 1120 of the hollow shaft 1110 and the proximal end 1125 oriented to the proximal end 1128 of the hollow shaft 1110 so that upon insertion the proximal end 1125 of microstent 1105 comprising the channel seals 1130 is located in the anterior chamber of the eye. In some preferred embodiments, the proximal end 1125 of the deployment device is connected to an ejector (not shown) that when actuated deploys the microstent from the deployment device. FIG. 11B provides a cross sectional view of the deployment device 1100 with the microstent 1105 with channels 1135 positioned in the hollow shaft 1110. The hollow shaft can be coupled to a deployment device or be part of the deployment device itself. Deployment devices that are suitable for use with the methods of the invention include but are not limited to the deployment devices described in U.S. Pat. Nos. 6,007,511, 6,544,249, and U.S. Publication No. US2008/0108933, the contents of each of which are hereby incorporated by reference in their entireties. The deployment device is preferably provided in a sterile package.

As indicated above, the secondary channels of the microstents of the present invention can be activated by a laser pulse focused on the thin membrane sealing the opening in the eye's anterior chamber. Intuitively, the laser procedure is similar to standard argon laser trabeculoplasty. This process is depicted schematically in FIG. 10, which shows a laser pulse being applied to ablate a sealed secondary channel in a microstent of the present invention.

Accordingly, in some embodiments, the present invention provides methods for treating glaucoma in a subject in need thereof comprising inserting a microstent of the invention into the eye of the subject so that fluid drains from the anterior chamber of the eye thereby reducing IOP. In some embodiments, the microstent is inserted by an ab interno approach. In some preferred embodiments, the microstent is placed so that the proximal end of the microstent comprising the channel seals is located in the anterior chamber of the eye and the distal end of the microstent is located so that fluid from the eye can ultimately drain into the subconjunctival space. In some preferred embodiments, the distal end is placed in the intra-Tenon's space.

In some embodiments, the methods of the present invention further comprise evaluating IOP after placement of the microstent. In some embodiments, if additional IOP reduction is required, the energy is applied to one or more of the seals to ablate or remove the seals to achieve the desired amount of IOP reduction. In some embodiments, the removal of the seals may be performed in a serial manner (i.e., one at a time) and IOP is measured after each seal is removed until the desired reduction in IOP is achieved. As described above, in preferred embodiments, the seals are removed by application of energy from a laser, such as an argon or YAG laser, although any other suitable means of removal of the seals may be employed.

References and citations to other documents, such as patents, patent applications, patent publications, journals, books, papers, web contents, have been made throughout this disclosure. All such documents are hereby incorporated herein by reference in their entirety for all purposes.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

EXAMPLE 1

A three-lumen glaucoma stent prototype was produced by Boston Micro Fabrication utilizing Projection Micro Stereolithography (POL) technology. The prototype was printed in HTL Resin, which has a translucent yellow colour. The membranes sealing two of three openings were printed as an integrated part of the stent and coloured post-print to absorb laser light. A slit lamp argon laser was then successfully used to individually puncture the membranes of the stent prototype.

EXAMPLE 2

A similar stent prototype as described in Example 1 was successfully implanted into an artificial eye from SimulEYE and a slit lamp argon laser was used to accurately puncture the membrane in gonioscopic view. A single laser pulse was sufficient to puncture one membrane. This experiment simulates the actual clinical procedure that uptitrates the pressure-lowering effect of the multilumen glaucoma stent.

What is claimed is:

1. A micro invasive glaucoma surgery (MIGS) microstent comprising:

a MIGS microstent with proximal and distal ends, the MIGS microstent having therein at least one open channel that extends between the proximal and distal ends, the at least one open channel having openings at both the proximal and distal ends to allow fluid flow therethrough, the MIGS microstent further having therein from 2 to 7 sealed channels that extend between the proximal and distal ends, the sealed channels having an opening at the distal end and a seal at the proximal end to prevent fluid flow therethrough, wherein the seal is a polymeric thin membrane configured for argon/YAG laser ablation.

2. The MIGS microstent of claim 1, comprising one open channel.

3. The MIGS microstent of claim 1, wherein the MIGS microstent comprises from 2 to 5 sealed channels.

4. The MIGS microstent of claim 3, comprising one open channel.

5. The MIGS microstent of claim 1, wherein the MIGS microstent comprises from 2 to 3 sealed channels.

6. The MIGS microstent of claim 5, comprising one open channel.

7. The MIGS microstent of claim 1, wherein the MIGS microstent comprises 2 sealed channels.

8. The MIGS microstent of claim 7, comprising one open channel.

9. The MIGS microstent of claim 1, wherein each of the channels are sized to provide a pressure difference of from 0.5 to 8.0 mm Hg across the channels.

10. The MIGS microstent of claim 1, wherein the channels are parallel.

11. The MIGS microstent of claim 1, wherein the proximal end of the MIGS stent comprises a rim portion that extends past the terminal ends of the channels.

12. The MIGS microstent of claim 1, wherein the MIGS stent is formed from a polymer.

13. The MIGS microstent of claim 12, wherein the polymer is selected from the group consisting of silicone, cross-linked polyvinyl alcohol (PVA) hydrogel, cross-linked PVA hydrogel foam, polyurethane, polyamide, styrene isobutylene-styrene block copolymer (Kraton), polyethylene terephthalate, polyester, polyorthoester, polyanhydride, polyether sulfone, polycarbonate, polypropylene, high molecular weight polyethylene, and polytetrafluoroethylene.

14. The MIGS microstent of claim 1, wherein the MIGS stent is formed from a gel material.

15. The MIGS microstent of claim 14, wherein the gel material is a cross-linked gelatin.

16. The MIGS microstent of claim 1, wherein the membrane is formed from a material selected from the group consisting of silicone, polyurethane, polyamide, styrene isobutylene-styrene block copolymer (Kraton), polyethylene terephthalate, polyester, polyorthoester, polyanhydride, polyether sulfone, polycarbonate, polypropylene, high molecular weight polyethylene, and polytetrafluoroethylene.

17. A method of treating glaucoma in a subject in need thereof comprising:

inserting a MIGS microstent of claim 1 into the eye of a subject so that the proximal end of the microstent is located in the anterior chamber of the eye and the distal end is located in a portion of eye allowing drainage into the subconjunctival space of the eye so that intraocular pressure in the anterior chamber is reduced due to the flow of fluid through the open channel of the MIGS microstent.

18. A deployment device comprising a MIGS microstent according to claim 1 inserted into a hollow shaft having a proximal end and a distal end.

* * * * *